United States Patent [19]
Plempel et al.

[11] Patent Number: 4,585,782
[45] Date of Patent: Apr. 29, 1986

[54] AZOLE DERIVATIVES ANTIMYCOTIC AGENTS WHICH RELEASE THE ACTIVE COMPOUNDS AT A RELATIVELY HIGH RATE

[75] Inventors: Manfred Plempel, Wuppertal; Manfred Bücheler, Overath; Wolfgang Gau; Erik Regel, both of Wuppertal; Karl H. Büchel, Burscheid; Hans-Jürgen Ploschke, Wuppertal, all of Fed. Rep. of Germany

[73] Assignee: Bayer Aktiengesellschaft, Leverkusen, Fed. Rep. of Germany

[21] Appl. No.: 581,527

[22] Filed: Feb. 21, 1984

Related U.S. Application Data

[63] Continuation of Ser. No. 374,553, May 3, 1982, abandoned, which is a continuation of Ser. No. 170,336, Jul. 21, 1980, abandoned.

[30] Foreign Application Priority Data

Aug. 11, 1979 [DE] Fed. Rep. of Germany ....... 2932691
Aug. 27, 1979 [DE] Fed. Rep. of Germany ....... 2934542

[51] Int. Cl.$^4$ .......................................... A61K 31/415
[52] U.S. Cl. .................................................. 514/396
[58] Field of Search ..................... 424/273 R; 514/396

[56] References Cited

U.S. PATENT DOCUMENTS 3,812,142  5/1974  Meiser et al. ...................... 424/269
4,038,409  7/1977  Walker et al. ...................... 424/273
4,038,410  7/1977  Rufer et al. ......................... 424/273
4,041,168  8/1977  Assandri et al. .................... 424/273
4,073,922  2/1978  Wyburn-Mason .............. 424/273 R
4,107,331  8/1978  Rosenberg ......................... 424/319
4,118,487  10/1978 Regel et al. ........................ 424/269
4,153,708  5/1979  Kramer et al. ..................... 424/273
4,233,311  11/1980 Kramer et al. ..................... 424/269
4,243,670  1/1981  Regel et al. ........................ 424/269

FOREIGN PATENT DOCUMENTS 741077  1/1970  Belgium .............................. 548/339

OTHER PUBLICATIONS

Burman; Principles of General Chemistry; 2/1969; pp. 207-209.

Primary Examiner—Allen J. Robinson
Attorney, Agent, or Firm—Sprung Horn Kramer & Woods

[57] ABSTRACT

The invention relates to antimycotic compositions comprising (1) an antimycotic effective amount of an azole derivative having antimycotic activity, said azole derivative being in the form of particles less than 4µ in size, (2) an acid and/or a buffer system consisting of an organic acid and a salt thereof to provide a pH of 3 to 4 or less in aqueous solution and (3) an inert pharmaceutical carrier. Also included in the invention are methods for the short term treatment of vaginal infections utilizing the compositions of the invention.

10 Claims, No Drawings

AZOLE DERIVATIVES ANTIMYCOTIC AGENTS WHICH RELEASE THE ACTIVE COMPOUNDS AT A RELATIVELY HIGH RATE

This is a continuation of application Ser. No. 374,553, filed 5/3/82, now abandoned, which is a continuation of Ser. No. 170,336 filed 7/21/80 (now abandoned).

The present invention relates to novel formulations of known antimycotic azole derivatives which release the active compounds at a relatively high rate and thus make short-term therapy possible.

Formulations of antimycotic azole derivatives in the form of vaginal tablets have already been disclosed for the treatment of fungal infections of the vagina. Using these formulations, a therapy time of 14 to 3 days is required for complete sanitisation of the vagina. This is to be attributed, inter alia, to the fact that the active compounds contained in the customary vaginal tablet formulations are only partly soluble in aqueous media. In order to shorten the therapy period, a higher rate of release of the active compounds in an aqueous medium is required, especially to eliminate the germs in the vaginal secretion. The known formulations are suitable for this purpose only to a limited extent because, of the available active compound present, only a small proportion dissolves in the volume of liquid in the vagina. Thus, if a shortening in the period of therapy, for example to one day, with a single administration, is to be achieved by further increasing the concentration of active compound, optimum release of the active compound must be ensured.

According to the present invention there is provided an antimycotic agent which contains an azole derivative having antimycotic action as the active compound and one or more tablet formulation auxiliaries in which the active compound in the form of particles less than 4μ in size and in which the agent also contains an acid and/or a buffer system consisting of an organic acid and a salt or salts thereof. The antimycotic agents of the present invention are formulated to make it possible for the active compound to be released at an optimum rate and thus make a shortened period of therapy of one day possible by achieving fungicidal concentrations of the active compound, for example clotrimazole.

This effect is achieved by reducing the pH value of the known formulations from 5 to 6 and over to 3 to 4 or less, in aqueous solution, the pH range of 3 to 4 being preferred. The increase in the release of active compound thereby achieved can be up to one power of ten. If a certain ionic concentration is furthermore also ensured, the solubility of the azole derivative is further increased by ionic bonding by virtue of the ionic strength. The preferred ionic strength here is between 0.1 to 0.8.

Active compounds which can be formulated in this manner are all the azole derivatives which have an antimycotic action (preferably imidazole derivatives and triazole derivatives).

The compounds of the following formulae may be mentioned as particularly preferred examples:

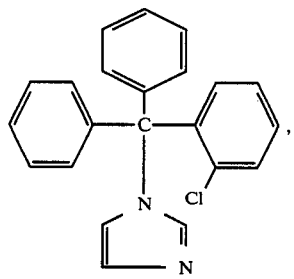

(I)

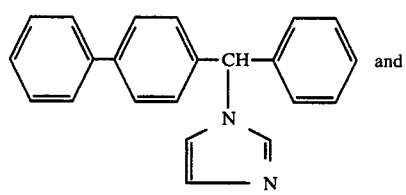

(II)

and

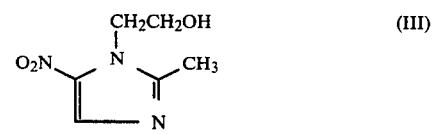

(III)

Numerous other azole derivatives having an antimycotic action are known from DE-OS (German Published Specification) 2,430,039 and DE-OS 2,461,406. It has been found, in particular, that vaginal tablet formulations which contain the compound of the formula (II) and also lactic acid and calcium lactate, or the compounds of the formulae (I) and (III) and also citric acid and primary sodium citrate, are so much better formulated that a single administration on one day can cure vaginal mycoses, especially those caused by species of *candida* and *torulopsis*. The compatibility of such formulations is completely satisfactory.

Other buffer systems and/or the acids or the acid salts by themselves also have the favourable effect mentioned on the formulations. Such systems can be: citric acid/primary Na citrate, lactic acid/Na lactate, DL-tartaric acid/KNa tartrate, adipic acid, ascorbic acid/the Na half-salt of ethylenediaminetetraacetic acid, fumaric acid, glycocoll buffer, potassium hydrogen phthalate buffer, tartrate buffer ($KHC_2H_4O_6$) and phosphate buffer. The ratios and the amounts of the components of the buffer systems are so chosen, that an acid $P_H$ value is maintained during the therapy.

The compositions according to the invention are administered in the form of tablets or of vaginal crems.

The compounds below are examples of tablet formulation auxiliaries in the present context which provide an inert pharmaceutical carrier. Starch, for example maize starch, rice starch, potato starch and wheat starch; and lactose, glucose, sucrose, microcrystalline cellulose, colloidal silicon dioxide, magnesium stearate, stearic acid, talc, polyvinylpyrrolidone (linear and crosslinked), sodium chloride, polyethylene glycol, hydroxypropylmethylcellulose, gelatin, Ca phosphates, cellulose, mannitol, sodium carboxymethyl-starch, sodium carbonate, sodium bicarbonate, calcium carbonate, sodium carboxymethylcellulose (linear and crosslinked) and magnesium carbonate.

For further tablet auxiliaries see "Die Tablette, Grundlagen und Praxis des Tablettierens, Granulierens und Dragierens" ("Tablets, the Principles and Practice of Tablet-making, Granulating and Coating") by W. A. Ritschel, pages 85-144, and "Katalog pharmazeutischer Hilfsstoffe" ("Catalogue of Pharmaceutical Auxiliaries"), compiled by a work group from Messrs. Ciba-Geigy, Hoffmann-La Roche and Sandoz, Basle 1974.

The following Examples illustrate the preparation of formulations according to the present invention.

EXAMPLE 1

500 g of active compound of the formula (I) are mixed, initially in the dry state, with the following amounts of tablet auxiliaries in a fluidised bed granulator: 190 g of citric acid, 195 g of primary Na citrate, 314 g of lactose, 148 g of maize starch, 230 g of micro-crystalline cellulose and 4 g of polyethylene glycol sorbitane oleate; the mixture is then granulated by spraying water in and the granules are dried. 34 g of Mg stearate and 85 g of crosslinked polyvinylpyrrolidone are then admixed to the granules and vaginal tablets with a total weight of 1,700 mg are formed from the mixture.

EXAMPLE 2

100 g of active compound of the formula II are mixed, in the dry state, with 140 g of lactic acid, 60 g of Ca lactate, 1,010 g of lactose and 238 g of maize starch in a planetary mixer, the mixture is granulated with a paste consisting of 50 g of maize starch and 300 g of water, the granules are dried in a fluidised bed drier, vacuum drier or circulating air drier, 17 g of Mg stearate and 85 g of crosslinked polyvinylpyrrolidone are then added and the mixture is pressed to vaginal tablets weighing 1,700 mg.

EXAMPLE 3

500 g of active compound of the formula (III) are mixed, in the dry state, with 831 g of lactose, 200 g of the Na half-salt of ethylenediaminetetraacetic acid, 126 g of maize starch, 4 g of colloidal silicon dioxide and 4 g of polyethylene glycol sorbitane oleate in a planetary mixer, the mixture is granulated with water in the same apparatus, the granules are dried in a fluidised bed in vacuo or in a circulating air drying cabinet, a further 39 g of Mg stearate are added to the granules obtained and the mixture is then pressed to vaginal tablets weighing 1,700 mg.

What is claimed is:

1. An antimycotic composition comprising (1) an antimycotic effective amount of an azole derivative selected from the group consisting of the compound of the formula

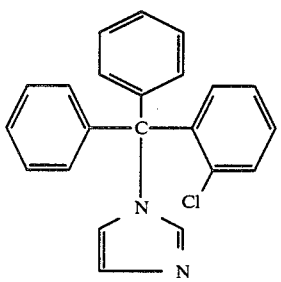

and the compound of the formula

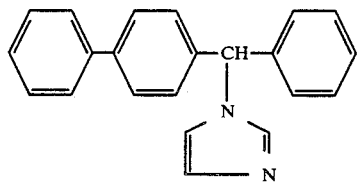

(2) an acid, a buffer system or a mixture thereof consisting of an acid and a salt thereof to provide a pH of 3 to 4 or less in aqueous solution and (3) an inert pharmaceutical carrier, said compositions having an ionic strength between 0.1 and 0.8.

2. An antimycotic composition according to claim 1, in which the compound of the formula

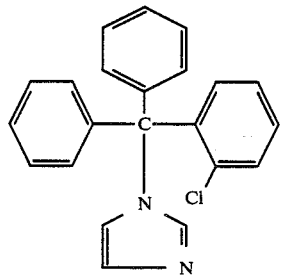

is the active compound.

3. An antimycotic composition according to claim 1 in which the compound of the formula

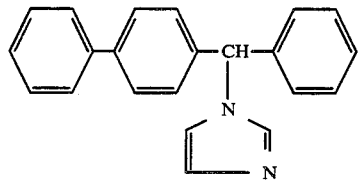

is the active compound.

4. An antimycotic composition according to claim 1, in which the buffer system consists of citric acid and primary sodium citrate.

5. An antimycotic composition according to claim 1 in which the buffer system consists of lactic acid and calcium lactate.

6. An antimycotic composition according to claim 1, wherein the azole derivative is in the form of particles less than $4\mu$ in size.

7. A method for the treatment of fungal infections of the vagina which comprises administering to the vaginal area an effective antimycotic amount of the composition of claim 1.

8. A method for the treatment of fungal infections of the vagina which comprises administering to the vaginal area an effective antimycotic amount of the composition of claim 2.

9. A method for the treatment of fungal infections of the vagina which comprises administering to the vaginal area an effective antimycotic amount of the composition of claim 3.

10. A method for the treatment of fungal infections of the vagina which comprises administering to the vaginal area an effective antimycotic amount of the composition of claim 4.

* * * * *